United States Patent
Chu et al.

(10) Patent No.: US 9,035,045 B2
(45) Date of Patent: May 19, 2015

(54) PROCESS FOR MANUFACTURING PARTIALLY CROSS-LINKED ALGINATE SOLUTION

(71) Applicant: Ikaria Development Subsidiary One LLC, Hampton, NJ (US)

(72) Inventors: Jennifer Hsing-Chung Chu, Ivoryton, CT (US); Joshua Shockey, Bend, OR (US)

(73) Assignee: Bellerophon BCM LLC, Hampton, NJ (US)

( * ) Notice: Subject to any disclaimer, the term of this patent is extended or adjusted under 35 U.S.C. 154(b) by 112 days.

(21) Appl. No.: 13/723,989

(22) Filed: Dec. 21, 2012

(65) Prior Publication Data

US 2013/0165403 A1     Jun. 27, 2013

Related U.S. Application Data

(60) Provisional application No. 61/578,613, filed on Dec. 21, 2011.

(51) Int. Cl.

| C08B 37/04  | (2006.01) |
| A61K 9/08   | (2006.01) |
| A61K 31/734 | (2006.01) |
| C08B 37/00  | (2006.01) |
| C08J 3/075  | (2006.01) |
| B01F 13/00  | (2006.01) |
| B01F 3/08   | (2006.01) |
| C08L 5/04   | (2006.01) |

(52) U.S. Cl.
CPC .................. *A61K 9/08* (2013.01); *A61K 31/734* (2013.01); *C08B 37/0084* (2013.01); *C08J 3/075* (2013.01); *B01F 13/0066* (2013.01); *B01F 3/0861* (2013.01); *B01F 3/088* (2013.01); *B01F 2215/0431* (2013.01); *B01F 2215/0477* (2013.01); *C08J 2305/04* (2013.01); *C08L 5/04* (2013.01); *B01F 13/0059* (2013.01)

(58) Field of Classification Search
None
See application file for complete search history.

(56) References Cited

U.S. PATENT DOCUMENTS

| 5,665,812    | A  * | 9/1997 | Gorce et al. ................... 524/495 |
| 7,909,502    | B2   | 3/2011 | Ehrfeld et al. |
| 2005/0003010 | A1   | 1/2005 | Cohen et al. |
| 2006/0083721 | A1 * | 4/2006 | Cohen et al. ................. 424/93.7 |
| 2011/0081677 | A1   | 4/2011 | Luo et al. |
| 2011/0129941 | A1   | 6/2011 | Kumacheva et al. |

FOREIGN PATENT DOCUMENTS

WO     WO-99/15211     4/1999

OTHER PUBLICATIONS

Capretto et al. Top Curr Chem (2011) 304: 27-68, published Apr. 28, 2011.*
"Modular Microreaction Technology", *Ehrfeld Mikrotechnik BTS GmbH* 2006, 26 pages.
Lee, Chia-Yen et al., "Microfluidic Mixing: A Review", *Int. J. Mol. Sci.*, 12 2011, pp. 3263-3287.
PCT International Preliminary Report on Patentability in PCT/US2012/071279, mailed Jul. 3, 2014, 8 pages.
PCT International Search Report and Written Opinion in PCT/US2012/071279, mailed Feb. 28, 2013, 13 pgs.
Kang, Edward et al., "Novel PDMS cylindrical channels that generate coaxial flow, and application to fabrication of microfibers and particles", *Lab Chip*, 10 2010, 1856-1861.
Liu, Xinxing et al., "Rheology characterization of sol-gel transition in aqueous alginate solutions induced by calcium cations through in situ release", *Polymer* 44 2003, 407-412.

* cited by examiner

*Primary Examiner* — Layla Bland
(74) *Attorney, Agent, or Firm* — Servilla Whitney LLC

(57) ABSTRACT

Described is a microfluidic process for manufacturing partially cross-linked alginate solution, wherein the alginate solution is a homogenous liquid which exhibits an elastic response (G') which is equal to or greater than its viscous response (G"). In particular, the process may comprise microfluidic mixing of sodium alginate and calcium gluconate solutions to provide an injectable partially cross-linked alginate solution.

17 Claims, 2 Drawing Sheets

PROCESS FOR MANUFACTURING PARTIALLY CROSS-LINKED ALGINATE SOLUTION

CROSS-REFERENCE TO RELATED APPLICATIONS

This application claims the benefit under 35 U.S.C. §119 (e) to U.S. Provisional Application No. 61/578,613, filed Dec. 21, 2011, the entire content of which is incorporated herein by reference in its entirety

TECHNICAL FIELD

Embodiments of the present invention generally relate to the field of processes for manufacturing injectable partially cross-linked alginate solutions.

BACKGROUND

Cross-linked polymer gel materials are widely utilized in the biomedical industry. For example, polysaccharide gels have been applied in contact lenses, blood contact materials, controlled release formulations, wound dressings, bioadhesives, membranes, superabsorbents, cell encapsulation and immunoisolation materials, and tissue engineering scaffolds.

The potential use of polysaccharide gel materials for treating damaged heart tissue has been intensively researched during the past decade.

The main focus of research has been on utilizing polysaccharide gels for treating the heart tissue following myocardial infarction. Myocardial infarction typically causes an acute loss of myocardial tissue and an abrupt increase in loading conditions which induces left ventricular remodeling. The early phase of left ventricular remodeling involves expansion of the infarct zone, which often results in early ventricular rupture or aneurysm formation. Late remodeling encompasses the entire left ventricle and involves time-dependent dilatation, recruitment of border zone myocardium into the scar, distortion of ventricular shape and mural hypertrophy. Consequently, it may lead to progressive deterioration in contractile function, heart failure and eventually death.

Accordingly, cessation or reversal of progressive chamber remodeling is an important aim of heart failure therapy. Clinical attempts to minimize the devastating effects of myocardial infarction have thus far failed to effectively repair the irreversible damage inflicted to the heart tissue.

Recently, attempts to implant living cells in damaged myocardium have given hope for repairing the damaged tissue via promoting tissue regeneration. This approach has advanced considerably with the development of 3-D biomaterial scaffolds aimed at supporting implantation of donor cells (e.g., cardiac cells or stem cells) in the myocardium. Lately, 3-D biomaterial scaffolds made of polysaccharide gel were successfully implanted onto damaged myocardium with promising results. However, clinical use of such cell seeded 3-D biomaterial scaffolds is limited due to scarcity of suitable donor cells and the high risk involved in major surgery.

One polysaccharide gel that has been investigated for treating damaged tissue is a partially cross-linked aqueous soluble formulation of sodium alginate and calcium cations. The partially cross-linked alginate solution may undergo a transition from liquid to gel in damaged body tissue with slightly elevated extracellular calcium concentration, thereby mechanically supporting the tissue. One particular application is for the treatment of tissue damaged by myocardial infarction, in which case the partially cross-linked alginate solution gels in the infarcted cardiac tissue and supports the weakened heart wall to prevent cardiac remodeling and subsequent congestive heart failure.

However, there is a need to provide improved processes for the manufacturing of injectable partially cross-linked alginate solutions that maintain a liquid state until they interact with damaged tissue.

SUMMARY OF THE INVENTION

One aspect of the present inventions relates to a process for preparing an alginate solution comprising providing a first aqueous solution comprising a monovalent alginate salt, providing a second aqueous solution comprising a divalent cation salt, and uniformly mixing the first aqueous solution and the second aqueous solution in a microfluidic process to provide a partially cross-linked homogenous liquid alginate solution. In one or more embodiments of this aspect, the alginate solution exhibits an elastic response (G') which is equal to or greater than its viscous response (G"). In some embodiments, the microfluidic process comprises multilamination.

According to one or more embodiments, the divalent cation salt comprises a calcium salt. In some embodiments, the calcium salt comprises calcium gluconate. One or more embodiments provide that the monovalent alginate salt comprises sodium alginate.

In one or more embodiments, the concentration of sodium alginate in the calcium alginate solution is from about 0.8 to about 1.5% w/v and the concentration of calcium gluconate in the calcium alginate solution is about 0.2 to about 0.4% w/v. In some embodiments, the alginate has a molecular weight ranging from about 10 to about 100 kDa.

Some embodiments provide that the method further comprises sterilizing the alginate solution. In one or more embodiments, sterilizing the alginate solution comprises sterile filtering.

According to one or more embodiments, the process is a continuous process. Some embodiments provide that the volumetric flow rate of the process is in the range of 0.05 to 5 L/min.

In one or more embodiments of the process, the characteristic mixing time ($\tau_m$) is less than a characteristic reaction time ($\tau_R$). In some embodiments, the process has a local mixing time less than 1 second. Further embodiments provide a local mixing time less than 0.1 seconds. In other embodiments, the process has a global mixing time less than 1 second. Some embodiments provide that the local mixing time and the global mixing time are less than 0.1 seconds.

Another aspect of the invention provides a process for preparing an alginate solution comprising providing a first aqueous solution comprising a monovalent alginate salt, providing a second aqueous solution comprising a calcium salt, and uniformly mixing the first aqueous solution and the second aqueous solution in a microfluidic mixing process to provide a partially cross-linked homogenous liquid alginate solution. In some embodiments of this aspect, the alginate solution exhibits an elastic response (G') which is equal to or greater than its viscous response (G") and the alginate solution comprises alginate in an amount ranging from 0.1 to 4% (w/v) with a molecular weight ranging from 1 to 300 kDa and calcium cations in an amount ranging from 0.02 to 0.04% (w/v). According to one or more embodiments of this aspect, the alginate salt comprises sodium alginate and the calcium salt comprises calcium gluconate.

In one or more embodiments, the microfluidic process comprises multilamination. Some embodiments provide that the process has a characteristic mixing time ($\tau_m$) less than a characteristic reaction time ($\tau_R$). In one or more embodiments, the process has a local mixing time less than 1 second.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
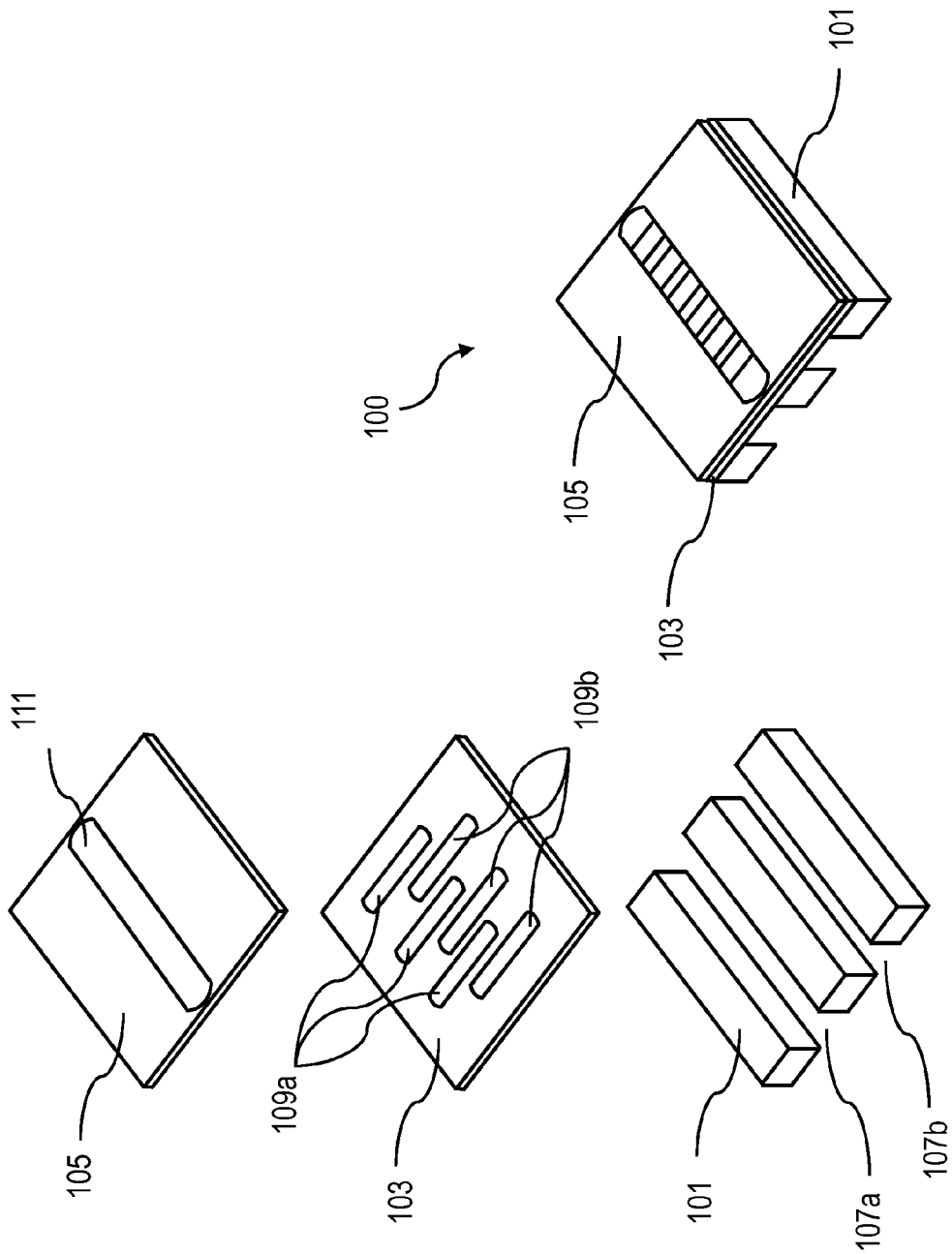
FIG. 1A depicts a schematic of a channel plate, mixing plate and aperture plate of a multilamination mixer in accordance with one or more embodiments of the invention.
FIG. 1B depicts a schematic of an assembled multilamination mixer in accordance with one or more embodiments of the invention and FIG. 2 depicts a schematic of a manufacturing process in accordance with one or more embodiments of the invention.

Previous attempts to produce large scales of partially cross-linked alginate solutions have resulted in inhomogeneous mixtures, particularly the presence of translucent sheets in the final alginate solution, which are believed to be sheets of gel. Such results were found in both batch and continuous processes, even with the use of homogenizers during the mixing of the component solutions. It has been found, however, that a microfluidic mixing process can be used to provide a partially cross-linked alginate solution without visible or detectable inhomogeneities.

Before describing several exemplary embodiments of the invention, it is to be understood that the invention is not limited to the details of construction or process steps set forth in the following description. The invention is capable of other embodiments and of being practiced or being carried out in various ways.

Unless indicated otherwise, all concentrations of mixtures or solutions are given as mass concentrations, which are defined as the mass of a constituent or solute divided by the volume of the mixture.

As used herein, the term "solution" refers to a liquid in which two or more substances (e.g. solute and solvent) are mixed together and uniformly dispersed. The phrase "aqueous solution" refers to a liquid in which one or more substances (solutes) are uniformly dispersed in water (solvent).

The terms "liquid" and "flowable" are used interchangeably herein and refer to the capacity of a substance to flow freely and assume the shape of the space containing it.

As used herein, the phrase "cross-linked polymer" refers to a network of polymer units being inter-linked via covalent, hydrogen or ionic bonding.

As used herein, the term "gel" refers to a semisolid colloidal suspension of a solid in a liquid. The term "hydrogel" refers to a gel which contains water as the liquid.

The term "alginate" refers to a polyanionic polysaccharide copolymer derived from sea algae (e.g., *Laminaria hyperborea, L. digitata, Eclonia maxima, Macrocystis pyrifera, Lessonia nigrescens, Ascophyllum codosum, L. japonica, Durvillaea antarctica,* and *D. potatorum*) and which includes β-D-mannuronic (M) and α-L-guluronic acid (G) residues in varying proportions.

One aspect of the invention relates to a microfluidic mixing process for uniformly mixing a first solution comprising an alginate salt and a second solution comprising a divalent cation salt. As used herein, a "microfluidic" mixing process refers to a process that mixes fluids on a "micro" scale. Typically, a micro scale refers to scales less than one millimeter. For a microfluidic mixing process, at least one characteristic dimension is in the range of 1 nm to 1 mm. According to one or more embodiments, a microfluidic process has characteristic dimensions less than or equal to 500 µm. In some embodiments, a microfluidic process has characteristic dimensions less than or equal to 100 µm. In some embodiments, a microfluidic process has characteristic dimensions less than or equal to 50 µm. In other embodiments, a microfluidic process has characteristic dimensions less than or equal to 10 µm. According to still other embodiments, a microfluidic process has characteristic dimensions less than or equal to 1 µm.

Microfluidic mixing may be accomplished in a variety of ways, including, but not limited to, multilamination of fluid streams, successive splitting and rearrangement of fluid flows, and colliding jets of fluids. According to one or more embodiments of the invention, the microfluidic process comprises multilamination. Multilamination is a process in which streams of fluid to be mixed are separately fanned out in a large number of thin lamellae. The lamellae of the two fluids are alternately arranged so that an interdigital configuration is generated. Due to diffusion and secondary flows, the molecules of the fluids mix rapidly to provide a uniform mixture.

FIG. 1A and FIG. 1B show an embodiment of a microfluidic multilamination mixer 100, also known as a "mixing cube." FIG. 1A depicts the multilamination mixer in three cross-sections to show the individual channel plate 101, mixing plate 103, and aperture plate 105. FIG. 1B shows the assembled multilamination mixer, with mixing plate 103 resting upon the channel plate 101, and the aperture plate 105 resting upon the mixing plate 103.

In FIG. 1A, channel plate 101 has feed channels 107a and 107b. When two fluids are to be mixed in the multilamination mixer, fluid A is introduced into feed channel 107a and fluid B is introduced into feed channel 107b. Mixing plate 103 is located directly above the channel plate 101. The slot openings 109a and 109b in mixing plate 103 are arranged in two rows such that slot openings 109a partially overlap channel 107and slot openings 109a are in fluid communication with channel 107a when the multilamination mixer is assembled. Likewise, slot openings 109b are arranged such that they partially overlap channel 107b and are in fluid communication with channel 107b when the multilamination mixer is assembled. In this way, fluid A and fluid B can be introduced into the multilamination mixer so that they do not mix in channel plate 101 or at the surface of mixing plate 103, but instead produce thin lamellae arranged in an interdigital configuration as the fluids flow upward through the stacked plates.

The widths of the slot openings 109a and 109b will determine the widths of the lamellae produced in the multilamination mixer. Thus, for the multilamination mixer in FIG. 1A, the characteristic dimension is the width of slot openings 109a and 109b. In one or more embodiments, the width of the slot openings is in the range of 1 μm to 500 μm. According to some embodiments, the width of the slot openings is in the range of 5 μm to 300 μm. In other embodiments, the width of the slot openings is in the range of 10 μm to 100 μm. In other embodiments, the width of the slot openings is in the range of 25 μm to 75 μm. According to still other embodiments, the width of the slot openings is in the range of 40 μm to 60 μm.

Aperture slot 111 is arranged so that it overlaps both sets of slot openings 107a and 107b. Once the fluids reach the aperture plate 105, the fluids rapidly mix in aperture slot 111.

Although the multilamination mixer is shown with three plates with a total of two channels, six slot openings and one aperture slot, persons having ordinary skill in the art will recognize that alternate configurations will not depart from the principles of a multilamination mixer. For example, a multilamination mixer may include additional channels, slot openings or aperture slots. Furthermore, the lengths of the channels and slots can be adjusted, as long as the slot openings are sufficiently narrow to provide thin lamellae so that the fluids can rapidly mix through diffusion and secondary flows.

Suitable multilamination mixers are commercially available from Ehrfeld Mikrotechnik BTS GmbH in Wendelsheim, Germany.

Another aspect of the invention relates to a process for preparing an alginate solution comprising uniformly mixing a first solution comprising an alginate salt and a second solution comprising a divalent cation salt. In embodiments of this aspect, the characteristic mixing time ($\tau_m$) is less than the characteristic reaction time ($\tau_R$). Although not wishing to be bound by any particular theory, it is believed that inhomogeneities and gel formation are a result of the cross-linking reaction occurring locally prior to the alginate and cation components being uniformly mixed.

The characteristic reaction time ($\tau_R$) is defined by:

$$\tau_R = \frac{1}{kC^{n-1}}$$

where k is the reaction rate constant, C is the reactant concentration and n is the reaction order.

For alginate cross-linking reactions, multimers of increasing chain length are formed in a series of consecutive reactions, which are generalized in the following reaction equations:

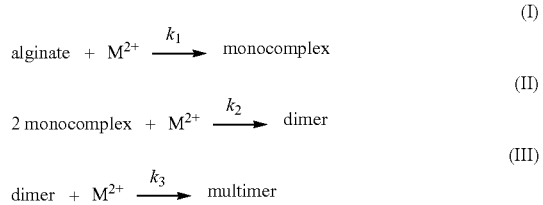

In reaction (I), an alginate chain and a divalent cation react to form a monocomplex. In reaction (II), two monocomplexes and a divalent cation react to form an alginate dimer. In reaction (III), dimers and divalent cations react to form multimers, which may result in gelation.

Furthermore, it is expected that the reaction time is longer as the product chain length increases.

The cross-linking reaction under typical reaction conditions is relatively fast, thus obtaining a uniform product using ordinary mixing means can be challenging. In order to obtain a uniformly cross-linked product, the components must be combined in such a way that they are uniformly distributed in the mixture on a faster time scale relative to the rate of the reaction(s).

In one or more embodiments, the characteristic mixing time ($\tau_m$) is the time between initial contact of the reactants and homogeneity of the mixture on a molecular scale. This mixing time can be characterized at either the local or global scale. At the local scale, mixing refers to homogeneous mixing of the reactants in the zone of initial contact. Global mixing time characterizes the time at which all the species that are in process are homogenous. In some embodiments, "global mixing time" is the same as the "blend time", which is the time required to reduce concentration fluctuations by 95%.

In processes where $\tau_R < \tau_m$, it is possible for cross-linking to occur and inhomogeneities to form, even though the concentrations of alginate and divalent cation are lower than the concentrations required for complete gelation.

Thus, one or more embodiments of the present invention provide a process for producing partially cross-linked alginate solution wherein $\tau_R > \tau_m$. By utilizing a process where the characteristic mixing time is less than the characteristic reaction time, a uniform partially cross-linked material may be produced. Some embodiments provide that the characteristic mixing time is much less than the characteristic reaction time such that $\tau_R \gg \tau_m$.

Therefore, one aspect of the invention involves mixing the solutions in such a manner that the mixing time is very short. In some embodiments, this characteristic mixing time is less than 1 second. In other embodiments, the characteristic mixing time is less than 0.1 seconds. Other embodiments provide a characteristic mixing time less than 0.01 seconds. Still other embodiments provide a characteristic mixing time less than 0.001 seconds. According to one or more embodiments, these short characteristic mixing times are achieved by using a microfluidic mixing process, such as a multilamination mixer.

In one or more embodiments, the characteristic mixing time is the local mixing time. In other embodiments, the characteristic mixing time is the global mixing time.

Figure 2:
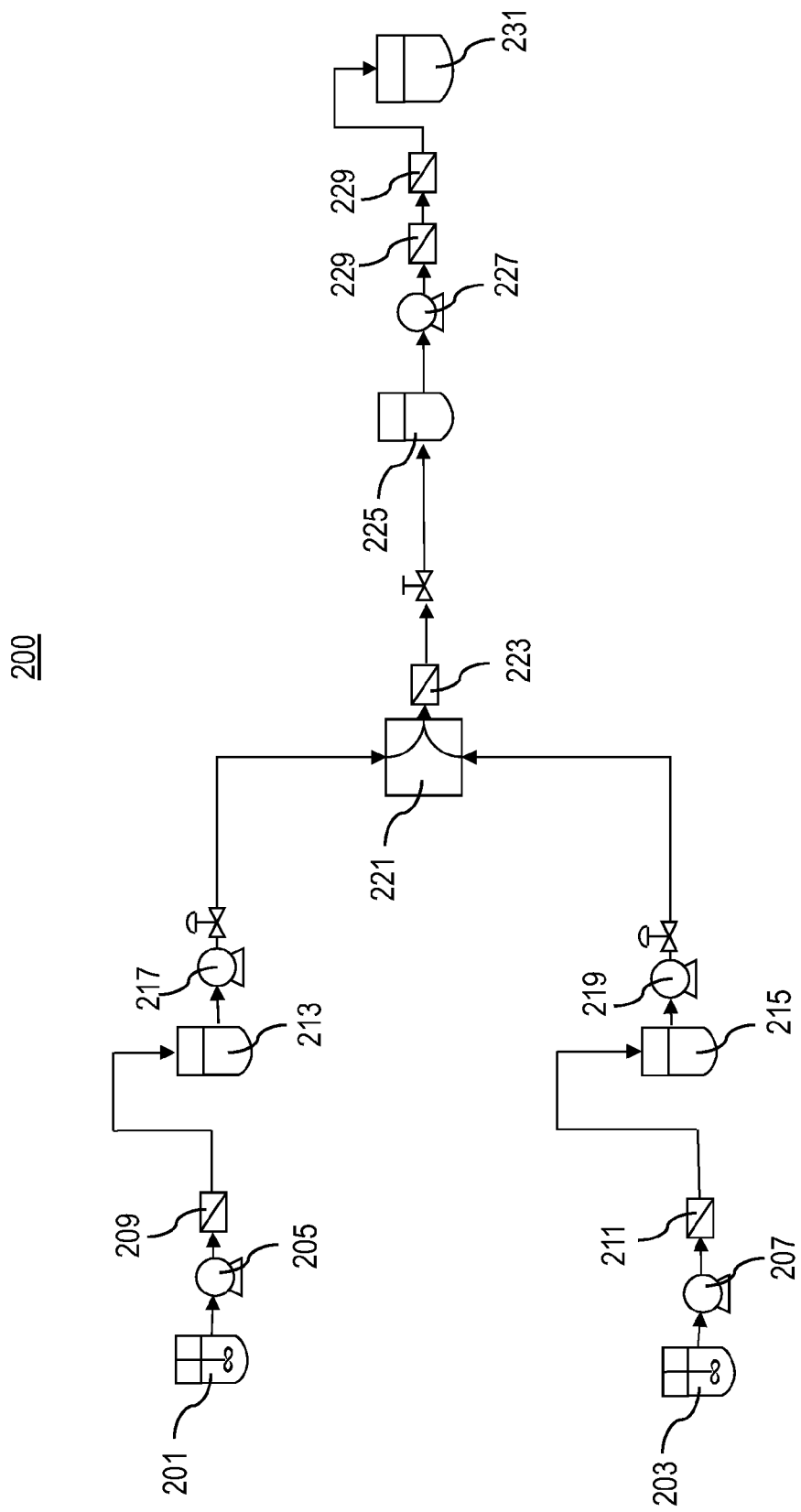

FIG. 2 shows a schematic of an embodiment of the manufacturing process 200 for providing a partially cross-linked alginate solution. In FIG. 2, the arrows indicate the direction of movement for the various aqueous solutions. Mixer 201 mixes the alginate salt with water to provide an alginate salt solution, such as 1.5 to 2.5% w/w sodium alginate. The alginate salt solution is then pumped by pump 205 through solution filter 209 to provide a filtered alginate salt solution, which is then stored in tank 213.

Mixer 203 mixes the divalent cation salt with water to provide a divalent cation salt solution such as 0.4 to 0.8% w/w calcium gluconate. The divalent cation salt solution is then pumped by pump 207 through solution filter 211 to provide a filtered divalent cation salt solution, which is then stored in tank 215.

According to one or more embodiments, the partially cross-linked alginate solution can be injected into the body for treating damaged tissue. In such embodiments, the water used for the alginate salt solution and the divalent cation salt solution is water for injection. Suitable water for injection will have controlled pH and osmolarity, such as a pH in the range of about 5 to about 7 and an osmolarity of about 0. The water for injection may be purified prior to mixing with the alginate salt and the divalent cation salt, such as by distillation or reverse osmosis.

Pumps 217 and 219 pump the filtered alginate salt solution and divalent cation salt solution, respectively, which are then introduced into the microfluidic mixer 221. Although the solutions are pumped into the multilamination mixer in FIG. 2, the solutions can be introduced into the multilamination mixer in various other ways, such as by capillary action. As shown in FIG. 2, the two aqueous solutions may be provided as constant streams, and the microfluidic mixing process can be a continuous process. In the microfluidic mixer 221, the alginate salt solution and divalent cation salt solution are uniformly mixed to provide a homogenous liquid alginate solution. The concentrations of the alginate salt and divalent cation salt, as well as the average molecular weights of the alginate polymers, are chosen so that the resulting aqueous solution has partial cross-linking of the alginate polymers, but still remains liquid and flowable.

Optionally, the partially cross-linked alginate solution can then passed through a polishing filter 223 to remove any resulting inhomogeneities for regulatory and safety purposes, even though some embodiments of the process as described herein can minimize the inhomogeneities in the partially cross-linked alginate solution. The partially cross-linked alginate solution is then collected in a product collection tank 225.

In some embodiments, it is desirable to have a sterile product suitable for use as an injectable polymer. Thus, the product can be sterilized, such as using pump 227 to pump the product through sterilization filters 229. Sterile filtering may comprise passing the partially cross-linked alginate solution through a membrane having a pore size in the range of 0.02 to 2 μm. In some embodiments, the partially cross-linked alginate solution may be passed through a membrane having a pore size in the range of 0.1 to 0.5 μm. The final product is then collected in tank 231 before filling into vials.

However, it may be expensive and burdensome to have all of the manufacturing equipment in a sterile environment. Thus, according to some embodiments, only a portion of the equipment is in a cleanroom of class 100, class 10 or class 1. In such embodiments, the sterilization and vial fill would be performed in a cleanroom meeting the standards of class 100, but it would not be necessary to have other steps, such as the microfluidic mixing, in a cleanroom meeting the standards of class 100. Instead, the microfluidic mixing and the preparation of the alginate salt solution and the divalent cation salt solution may be performed in cleanrooms that meet the standards of class 100,000, class 10,000, or class 1,000. In a specific embodiment, the microfluidic mixing and/or the preparation of the alginate salt solution and the divalent cation salt solution are performed in cleanrooms meeting the standards of class 10,000.

By using a microfluidic mixer that utilizes multilamination or similar principles, the volume of the product manufactured may be scaled up by increasing the number microstructures instead of increasing the size of the characteristic dimensions. Therefore, instead of increasing the width of the slot openings in the multilamination mixer, the number of slot openings in the plates of the multilamination mixer may be increased or the number of multilamination mixers may be increased, thus preserving the advantages of the micro scales. Alternatively, the length of the slot openings may be increased, as long as the width of the slot openings is sufficiently narrow to provide thin lamellae of fluids.

Thus, high flow rates of microfluidic mixing are possible, and according to one or more embodiments the manufacturing process has a volumetric flow rate at a commercial scale rather than a laboratory scale. In one or more embodiments, the volume of partially cross-linked alginate solution produced is in the range of 0.05 to 5 L/min. The volumetric flow rate may even be scaled above 5 L/min, such as up to 10 L/min, 20 L/min or even 50 L/min. In some embodiments, the volume of partially cross-linked alginate solution produced is in the range of 0.2 to 3 L/min. In some embodiments, the volume of partially cross-linked alginate solution produced is in the range of 0.5 to 2 L/min The alginate salt may be any pharmacologically acceptable alginate salt. Examples of such alginate salts include, but are not limited to, monovalent alginate salts such as sodium, potassium, lithium, rubidium, cesium and ammonium salts of alginic acid. The alginate salt may also be a soluble alginate of an organic base such as a mono-, di-, or tri-ethanolamine alginate, aniline alginate, and the like. In some embodiments, the alginate salt comprises sodium alginate.

In accordance with one or more embodiments, the alginate has a monomer ratio between α-L-guluronic acid and β-D-mannuronic ranging between 1:1 to 3:1. In some embodiments, the monomer ratio is between 1.5:1 and 2.5:1. In some embodiments, the monomer ratio is about 2:1.

One or more embodiments provide that the alginate has a molecular weight ranging between 1 to 300 kDa. In some embodiments, the molecular weight is between 5 to 200 kDa. Further embodiments provide that the molecular weight of the alginate is between 10 to 100 kDa. In some embodiments, the alginate molecular weight is between 20 to 50 kDa.

Examples of divalent cation salts for partial cross-linking the alginate polymers are salts of calcium, strontium, barium and magnesium. According to one or more embodiments, the divalent cation salt comprises a calcium salt. Pharmacologically acceptable calcium salts include, but are not limited to, calcium gluconate, calcium citrate, calcium acetate, calcium fluoride, calcium phosphate, calcium tartrate, calcium sulfate, calcium borate and calcium chloride. In some embodiments, the calcium salt comprises calcium gluconate. The calcium gluconate salt may be either anhydrous or in hydrate form.

According to one or more embodiments, the partially cross-linked alginate solution exhibits an elastic response which is equal to or greater than its viscous response under small deformation oscillatory frequencies in the linear viscoelastic limit and a shear thinning behavior in a power-law relationship.

The term "viscosity ($\eta$)" used herein refers to a measure of the resistance of a fluid to flow. It is defined as the ratio of shear stress ($\tau$) to shear rate ($\gamma$):

$$\eta = \tau/\gamma$$

When the fluid obeys the equation for all shear rates, it is denoted a Newtonian fluid.

The viscoelastic properties of the composition can be determined by applying a sinusoidal stress or strain of frequency f to the sample and measuring the response. The response is divided into (i) an elastic part in phase with the applied stress or strain, and (ii) a viscous part out of phase. Because of the two components, a complex notation is used. The complex shear modulus is denoted by $G^*$, which is defined by the following formula:

$$G^* = G' + jG''$$

wherein $G'$ is the storage modulus, i.e., the elastic part, $G''$ is the loss modulus, i.e. the viscous part, and $j^2 = -1$.

The shear modulus as a function of frequency can be expressed by the slope n in a log-log plot of G' versus frequency, f, denoted by the following formula:

$$\text{Log } G' = n \log f + K$$

wherein K is a constant. In a physical gel n>0, and in a covalent gel n=0.

Viscoelastic features can be presented in terms of the storage modulus G' (herein referred to as the "elastic response") and the loss modulus G" (herein referred to as the "viscous response") as a function of angular frequency.

The values of elastic response (G'), viscous response (G') and viscosity ($\eta$) can be determined using standard rheological methods. According to one or more embodiments, the rheological measurements are obtained under an oscillatory frequency ranging within the viscoelastic limit. In some embodiments, the rheological measurements are obtained under an oscillatory frequency ranging between 0.01 and 100 Hz. In further embodiments, the rheological measurements are obtained under an oscillatory frequency ranging between 0.1 to 10 Hz.

Partially cross-linked alginate solutions may not have permanent cross links, are strongly frequency dependent and have G'-G" crossover. This is why the partially cross-linked alginate solution behaves as a liquid, but will gel when exposed to elevated calcium levels in damaged tissue.

The partially cross-linked alginate solutions are described in detail in US Patent Publication Nos. 2005/0003010 and 2006/0083721, the disclosures of which are hereby incorporated by reference in their entireties.

Table 1 below shows the fluidity and rheological characteristics of various homogenized mixtures of sodium alginate and calcium gluconate.

TABLE 1

Visual appearance and rheological characteristics of homogenized mixtures of sodium alginate and calcium gluconate

| Alginate Average Mw (kDa) | Sodium Alginate Conc. (% w/v) | Calcium Gluconate Conc. (% w/v) | Visual Appearance | Rheological Characteristics | $Ca^{2+}$ Conc. (% w/v) |
|---|---|---|---|---|---|
| 15 | 1 | 0.4 | Flowable solution | G' ≥ G" | .03724 |
| 30 | 1 | 0.3 | Flowable solution | G' ≥ G" | .02793 |
| 30 | 0.8 | 0.3 | Flowable solution | G' ≥ G" | .02793 |
| 30 | 1.5 | 0.3 | Flowable solution | G' ≥ G" | .02793 |
| 100 | 1 | 0.270 | Flowable solution | G' ≥ G" | .02514 |
| 100 | 1 | 0.275 | Flowable solution | G' ≥ G" | .02560 |
| 100 | 1 | 0.3 | Flowable solution | G' ≥ G" | .02793 |

* G' = elastic response; G" = viscous response.

Mixtures of sodium alginate and calcium gluconate at a ratio ranging between about 1:0.4 to 1:0.3 developed into stable solutions which remained freely flowable for at least 24 hr at room temperature and for at least 30 days at 4-8° C. Such behavior is typical of medical solutions that can be injected into the bloodstream, even after long periods of time after mixing, but will form gels in damaged tissue.

Therefore, stable partially cross-linked alginate solutions can be freely flowable liquids and exhibit elastic responses which are equal to or greater than their viscous response under small deformation oscillatory frequencies in the linear viscoelastic limit.

In one or more embodiments, the concentration of alginate in the alginate salt solution prior to mixing with the divalent cation salt solution is in the range of 0.2 to 8% w/v. In some embodiments, the concentration of alginate in the alginate salt solution is in the range of 1 to 4% w/v. In some embodiments, the concentration of alginate in the alginate salt solution is in the range of 1.5 to 3% w/v. In some embodiments, the concentration of alginate in the alginate salt solution is in the range of 1.5 to 2.5% w/v.

One or more embodiments provide that the concentration of divalent cation in the divalent cation salt solution prior to mixing with the alginate salt solution is in the range of 0.01 to 0.2% w/v. In some embodiments, the concentration of divalent cation in the divalent cation salt solution is in the range of 0.02 to 0.1% w/v. In some embodiments, the concentration of divalent cation in the divalent cation salt solution is in the range of 0.04 to 0.08% w/v. In some embodiments, the concentration of divalent cation in the divalent cation salt solution is in the range of 0.05 to 0.07% w/v.

The ratio of alginate salt solution to divalent cation salt solution will depend on the concentrations of the corresponding solutions. According to some embodiments, the ratio of alginate salt solution to divalent cation salt solution is in the range of 0.1 to 10. In other embodiments, the ratio of alginate salt solution to divalent cation salt solution is in the range of 0.2 to 5. Other embodiments provide that the ratio of alginate salt solution to divalent cation salt solution is in the range of 0.4 to 2.5. Still other embodiments provide a ratio of alginate salt solution to divalent cation salt solution in the range of 0.5 to 2. In some embodiments, the ratio of alginate salt solution to divalent cation salt solution in the range of 0.7 to 1.5.

According to one or more embodiments, the final concentration (w/v) of alginate in the partially cross-linked alginate solution is in the range of 0.1 to 4%. In further embodiments, the final concentration (w/v) of alginate in the mixture is in the range of 0.5 to 2%. In some embodiments, the final alginate concentration is in the range of 0.8 to 1.5% w/v.

One or more embodiments of the present invention provide that the final concentration (w/v) of divalent cations in the mixture is in the range of 0.005 to 0.1%. In some embodiments, the final divalent cation concentration in the mixture is in the range of 0.01 to 0.05% w/v. Further embodiments provide that the divalent cation concentration is in the range of 0.02 to 0.04% w/v. In some embodiments, the divalent cation concentration is in the range of 0.025 to 0.035% w/v.

When calcium gluconate and sodium alginate are used as the divalent cation salt and alginate salt, respectively, some embodiments provide that the weight ratio between calcium gluconate and sodium alginate in the partially cross-linked alginate solution ranges between 2:1 and 1:10. According to one or more embodiments, the weight ratio is between 1:1 and 1:6. Further embodiments provide that the weight ratio is between 1:2 and 1:5. In some embodiments, the weight ratio is between 1:3 and 1:4.

According to one or more embodiments, the partially cross-linked alginate solution has uniform cross-linking between the alginate polymers. As used herein, the phrase "uniform cross linking" refers to spreading the bonds linking the polymer chains in a substantially non-clustered distribution. In some embodiments, uniform cross-linking is a substantially random distribution or even a substantially even distribution. The uniformly crossed-linked solution assumes substantial viscoelasticity yet retains its liquidity and flowability.

According to one or more embodiments, the partially cross-linked alginate solution produced by the process (i) maintains a liquid state in storage at room temperature for at least 24 hours and (ii) assumes a gel state following deposition within damaged body tissue. In some embodiments, the partially cross-linked alginate solution produced by the process maintains a liquid state in contact with blood when injected into a blood vessel, flows freely within the blood vessel, and assumes a gel state only upon coming into contact with damaged body tissue.

In some embodiments, the partially cross-linked alginate solution produced by the process is storage stable, i.e., it maintains its liquid solution form and syringeability for long periods of time. According to one or more embodiments, the partially cross-linked alginate solution is stable at room or lower than room temperature for a period of at least 24 hours. In some embodiments, the partially cross-linked alginate solution is stable at room or lower than room temperature for a period of at least 7 days. In other embodiments, the partially cross-linked alginate solution is stable at room or lower than room temperature for a period of at least 30 days. Other embodiments provide that the partially cross-linked alginate solution is stable at room or lower than room temperature for a period of at least one year. In yet another embodiment, the partially cross-linked alginate solution is stable at room or lower than room temperature for a period of at least 5 years.

In addition to being stable in storage, according to one or more embodiments, the partially cross-linked alginate solution maintains a liquid state within a blood vessel after being introduced via infusion or catheterization. In some embodiments, the partially cross-linked alginate solution can spread throughout the bloodstream. According to some embodiments, the partially cross-linked alginate solution can spread out of the blood vessel and into damaged tissue, where the solution then forms a gel. Thus, some embodiments provide that the partially cross-linked alginate solution can flow within a blood vessel, cross out of blood capillaries and spread into the extracellular matrix of the surrounding tissue.

One or more embodiments provide that the partially cross-linked alginate solution can be administered into body tissue via a needle. In some embodiments, the partially cross-linked alginate solution can be administered through a needle with an 18-27 gauge bore.

Following deposition within a damaged body tissue, the partially cross-linked alginate solution may form a gel state. In some embodiments, once gelatinized, the viscoelastic material provides substantial mechanical support and elasticity to the body tissue, as well as scaffolding for new tissue regeneration.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments. The order of description of the above method should not be considered limiting, and methods may use the described operations out of order or with omissions or additions.

It is to be understood that the above description is intended to be illustrative, and not restrictive. Many other embodiments will be apparent to those of ordinary skill in the art upon reviewing the above description. The scope of the invention should, therefore, be determined with reference to the appended claims, along with the full scope of equivalents to which such claims are entitled.

What is claimed is:

1. A process for preparing a partially cross-linked homogenous liquid alginate solution that maintains a liquid state in storage at room temperature for at least 24 hours comprising:
    providing a first aqueous solution comprising a monovalent alginate salt;
    providing a second aqueous solution comprising a divalent cation salt; and
    uniformly mixing the first aqueous solution and the second aqueous solution in a microfluidic multilamination mixing process to provide the partially cross-linked homogenous liquid alginate solution,
    wherein the alginate has a molecular weight ranging from about 10 to about 100 kDa, the alginate concentration in the partially cross-linked homogenous liquid alginate solution is in the range of 0.8 to 1.5% w/v, and the divalent cation concentration in the partially cross-linked homogenous liquid alginate solution is in the range of 0.02 to 0.04% w/v.

2. The process of claim 1, wherein the divalent cation salt comprises a calcium salt.

3. The process of claim 2, wherein the monovalent alginate salt comprises sodium alginate and the calcium salt comprises calcium gluconate.

4. The process of claim 3, wherein the concentration of calcium gluconate in the partially cross-linked alginate solution is about 0.2 to about 0.4% w/v.

5. The process of claim 1, further comprising sterilizing the partially cross-linked alginate solution after mixing.

6. The process of claim 5, wherein sterilizing comprises sterile filtering.

7. The process of claim 1, wherein the process is a continuous process.

8. The process of claim 7, wherein the volumetric flow rate of the process is in the range of 0.05 to 5 L/min.

9. The process of claim 1, wherein the process has a characteristic mixing time ($\tau_m$) less than a characteristic reaction time ($\tau_R$).

10. The process of claim 1, wherein the process has a local mixing time less than 1 second.

11. The process of claim 10, wherein the local mixing time is less than 0.1 seconds.

12. The process of claim 10, wherein the process has a global mixing time less than 1 second.

13. The process of claim 12, wherein the local mixing time and the global mixing time are less than 0.1 seconds.

14. A process for preparing a partially cross-linked homogenous liquid alginate solution that maintains a liquid state in storage at room temperature for at least 24 hours comprising:
    providing a first aqueous solution comprising a monovalent alginate salt;
    providing a second aqueous solution comprising a calcium salt; and
    uniformly mixing the first aqueous solution and the second aqueous solution in a microfluidic multilamination mixing process to provide a partially cross-linked homogenous liquid alginate solution which comprises alginate in an amount ranging from 0.8 to 1.5% w/v with a molecular weight ranging from about 10 to about 100 kDa and calcium cations in an amount ranging from 0.02 to 0.04% (w/v).

15. The process of claim 14, wherein the alginate salt comprises sodium alginate and the calcium salt comprises calcium gluconate.

16. The process of claim 14, wherein the process has a characteristic mixing time ($\tau_m$) less than a characteristic reaction time ($\tau_R$).

17. The process of claim 14, wherein the process has a local mixing time less than 1 second.

\* \* \* \* \*